United States Patent [19]
Harmon

[11] Patent Number: 5,935,157
[45] Date of Patent: Aug. 10, 1999

[54] THERAPEUTIC COLD PACK FOR HAND, WRIST AND FOREARM

[76] Inventor: Susan Harmon, 15 Tamalpais Ave., Belvedere, Calif. 94920

[21] Appl. No.: 08/933,289

[22] Filed: Sep. 18, 1997

[51] Int. Cl.⁶ ........................................................ A61F 7/00
[52] U.S. Cl. ............................. 607/111; 607/108; 607/114
[58] Field of Search ............................ 607/104, 108–112, 607/114; 165/46; 126/204; 602/2

[56] References Cited

U.S. PATENT DOCUMENTS

| | | | |
|---|---|---|---|
| 3,621,191 | 11/1971 | Cornwell | 607/111 X |
| 3,913,559 | 10/1975 | Dandliker . | |
| 4,856,294 | 8/1989 | Scaringe et al. . | |
| 4,964,402 | 10/1990 | Grim et al. | 607/111 X |
| 5,050,596 | 9/1991 | Walasek et al. | 607/111 |
| 5,369,807 | 12/1994 | Cho et al. | 607/111 X |
| 5,415,222 | 5/1995 | Colvin et al. . | |

OTHER PUBLICATIONS

Advertisement brochure "Now a Temperature Regulated Therapeutic Cold Pack for your Hand, Wrist and Forearm", le Mitt Therapeutic Cold Pack for Hand, Wrist and Forearm, S. Harman, Sausalito, CA.

Advertisement brochure "Now a Temperature Regulated Therapeutic Cold Pack for your Hand, Wrist and Forearm", le Mitt Therapeutic Cold Pack for Hand, Wrist and Forearm, S. Harman, Tiburon, CA.

Le Mitt Therapeutic Cold Pack for Hand, Wrist and Forearm Retail/Wholesale Price List/Order Form, S. Harman, Sausalito, CA.

Primary Examiner—Jeffrey R. Jastrzab
Assistant Examiner—Ryan Carter
Attorney, Agent, or Firm—Wigman, Cohen, Leitner & Myers, PC

[57] ABSTRACT

A device which is shaped like a mitt or glove and has surfaces for covering the palm and back of the human hand. Each of the palm and back surfaces is formed as a plenum which is filled with a heat exchange material. The heat exchange material is selected to provide cooling over a reasonably extended period of time, at an appropriate therapeutic temperature. The heat exchange material is preferably a phase change material such as a paraffinic phase change material having a phase change temperature on the order of 50° F. However, other temperatures and materials are contemplated. The mitt or glove is made of a flexible plastic sheet material such as a tripolymer material or polypropylene. The mitt is formed of four die cut sheets of the plastic sheet material which are shaped in the pattern of the outline of a human hand and forearm. The patterned sheets are stacked together and heat sealed together along their periphery. An opening is left between the palm plenum and back of the hand plenum so that the hand can be inserted into the mitt. Plenums are formed between the inner sheets and outer sheets which are left with filling openings through which the heat exchange is filled. The filling openings are then heat sealed.

7 Claims, 2 Drawing Sheets

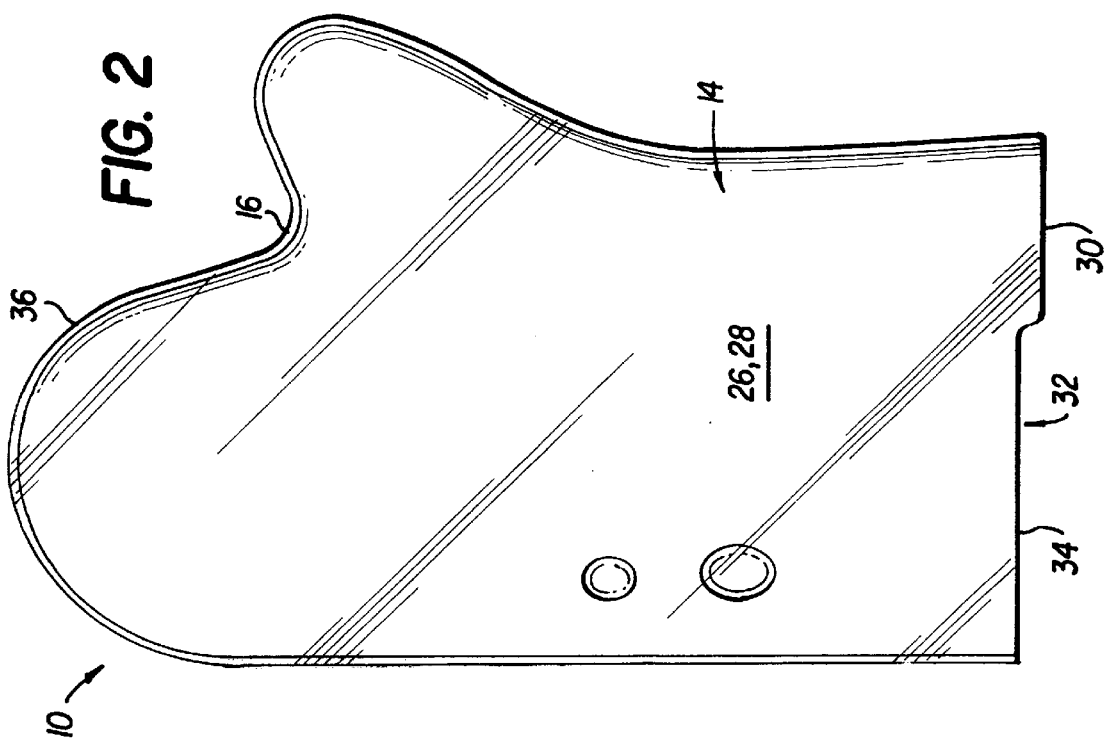
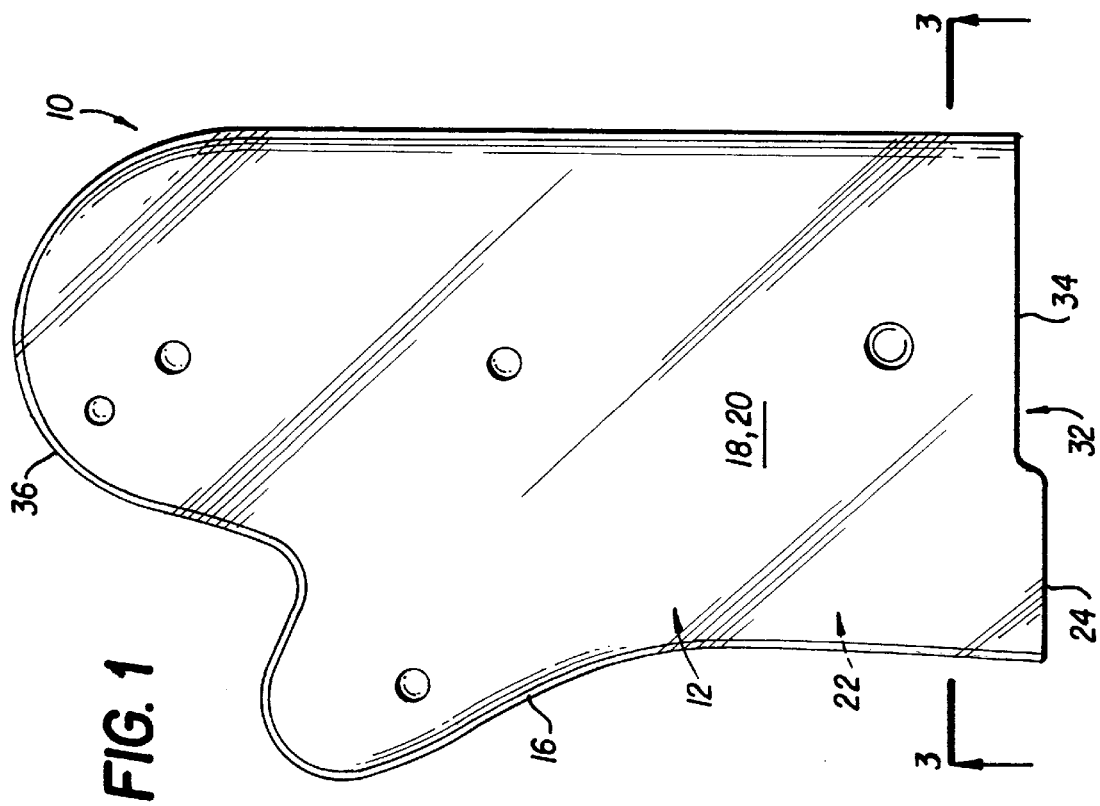

THERAPEUTIC COLD PACK FOR HAND, WRIST AND FOREARM

TECHNICAL FIELD

The present invention is directed to a device for applying a therapeutic cooling effect to the hand, wrist and forearm. More particularly, the invention is directed to a mitt or glove which fits over the hand, wrist and forearm and applies a cooling effect.

BACKGROUND OF THE INVENTION

Certain activities such as therapeutic massage or other extended use of the hands and fingers, such as sports or playing the piano, can result in muscular aches and pains. The application of cooling temperatures to the hands, wrist and forearm serves to provide relief from these aches and pains. Typical cold packs must be manually held in place and thus are not convenient to use, especially if relief is sought over brief intervals, such as between therapeutic massage sessions.

As explained below, the present invention overcomes the shortcomings of the prior art.

SUMMARY OF THE INVENTION

The present invention is directed to a device which is shaped like a mitt or glove and has surfaces for covering the palm and back of the human hand. Each of the palm and back surfaces is formed as a plenum which is filled with a heat exchange material. The heat exchange material is selected to provide cooling over a reasonably extended period of time, at an appropriate therapeutic temperature. The heat exchange material is preferably a phase change material such as a paraffinic phase change material having a phase change temperature on the order of 50° F. However, other temperatures and materials are contemplated. The mitt or glove is made of a flexible plastic sheet material such as a tripolymer material or polypropylene. The mitt is formed of four die cut sheets of the plastic sheet material which are shaped in the pattern of the outline of a human hand and forearm. The patterned sheets are stacked together and heat sealed together along their periphery. An opening is left between the palm plenum and back of the hand plenum so that the hand can be inserted into the mitt. Plenums are formed between the inner sheets and outer sheets which are left with filling openings through which the heat exchange is filled. The filling openings are then heat sealed.

BRIEF DESCRIPTION OF THE DRAWINGS

FIGS. 1 and 2 shows palm and back of the hand plan views of a device in accordance with the invention;

DETAILED DESCRIPTION OF THE INVENTION

Figure 3:
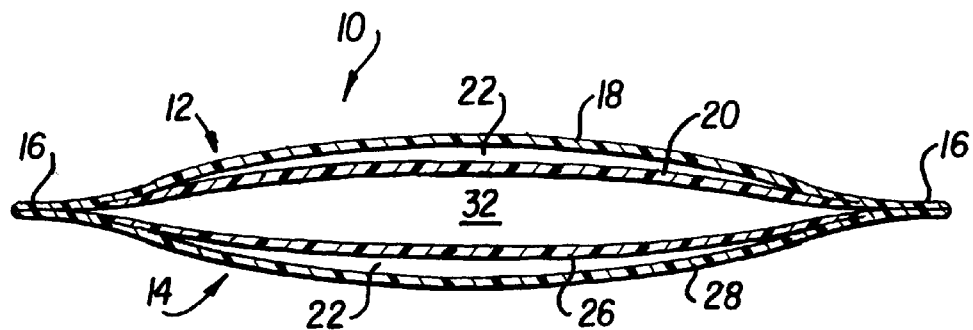
FIG. 3 is a cross-sectional view of the device taken along line 3—3 of FIG. 1.

Referring now to the drawings, wherein like elements are designated by like numerals throughout, FIGS. 1 and 2 show a device in the form of a mitt 10 having back side 12 and a palm side 14. The mitt 10 has heat seal 16 around the periphery of the mitt. Back side 12 is formed of two sheets 18, 20 which are filled with a phase change material 22 through filling port 24. Palm side 14 is similar to back side 12 and is formed of two sheets, 26, 28 which are also filled with a phase change material 22 through filling port 30. The filling ports 24, 30 are heat sealed to keep the phase change material inside. Opening 32 is provided at the end 34 of the mitt 10 opposite the finger tip end 36.

FIG. 3 is a cross-sectional view of the device 10 in accordance with the invention, showing the relative positions of the plastic sheets and phase change material.

Figure 4:
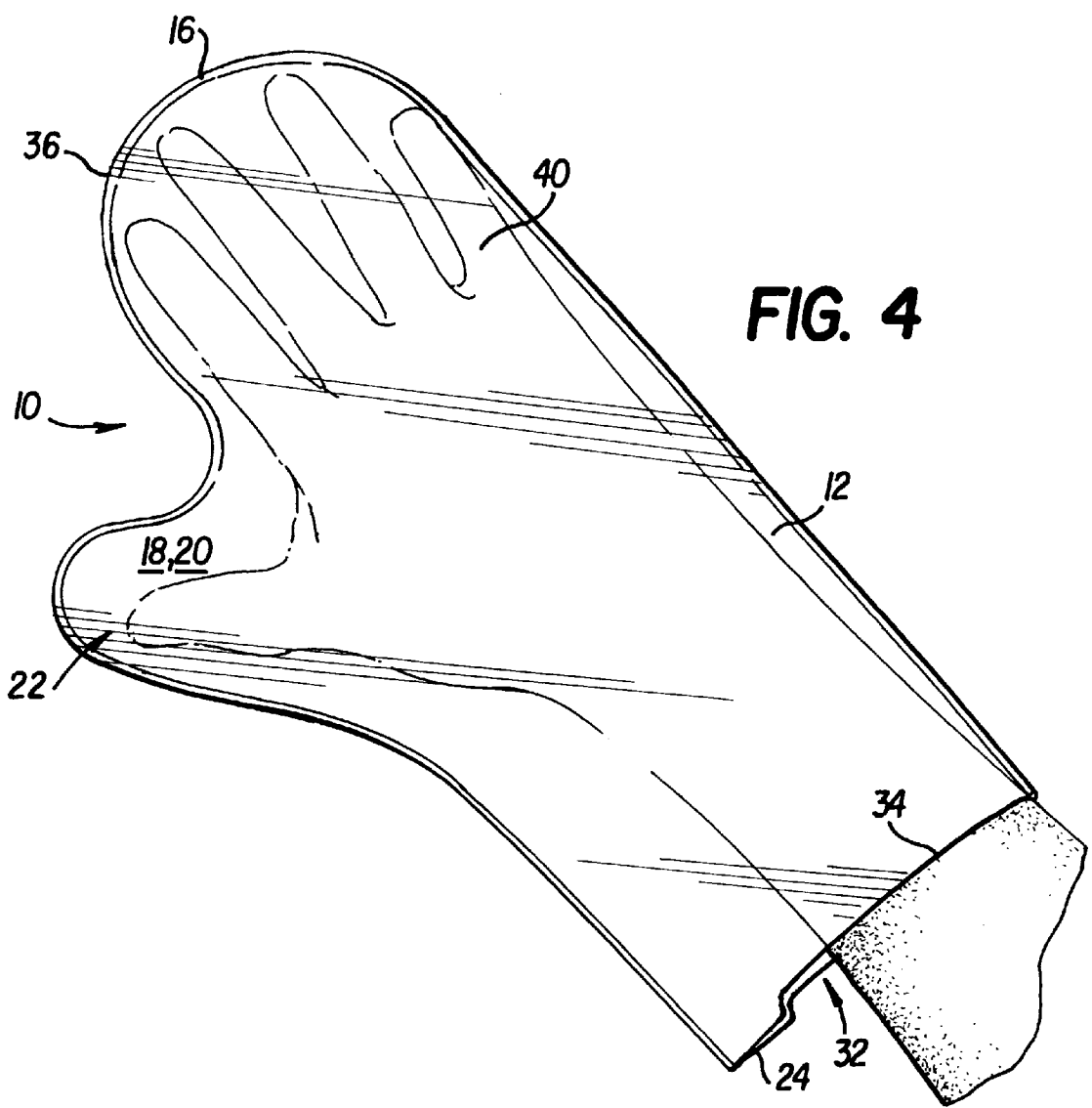
FIG. 4 shows an environmental perspective view of a device in accordance with the invention.

FIG. 4 shows mitt 10 in use. A hand 40 is inserted in opening 32, such that the hand, wrist and forearm are subjected to therapeutic cooling.

In operation, the mitt 10 is placed in a refrigerator, freezer, cooler or other cooling environment having a temperature lower than the phase change material 22 of the mitt 10. As a consequence, the phase change material 22 freezes. Once the mitt 10 is removed from the cooling environment, the temperature of the mitt 10 will rise by sensible heat addition until it reaches the phase change temperature of material 22. At that point, phase change material 22 will be in its solid phase. Thereafter, the temperature (cooling/freezing) remains constant until the phase change material has melted entirely. In use, the hand, wrist and forearm are subjected to a therapeutic cooling. Because of the shape of this mitt, it can be interchanged between the right and left hands.

The phase change material is preferably a proprietary mixture of paraffinic phase change materials, having a phase change temperature on the order of 50° F. Such proprietary phase change material mixture is available from Exothermal Technology Corporation, Melbourne, Fla. The plastic sheet material is preferably a tripolymer material or can be polypropylene or any other flexible sheet material which is heat sealable and compatible with the phase change material and also compatible with thermal cycling by repeated freezing and thawing. Suitable plastic material is available from PB Plastics, Mims, Fla.

Typical heat exchange materials and flexible sheet materials are disclosed in U.S. Pat. No. 3,913,559 to Dandliker, U.S. Pat. No. 4,856,294 to Scaringe et al, and U.S. Pat. No. 5,415,222 to Colvin et al, the disclosures of which are hereby incorporated by reference herein.

While a phase change material is preferred, gels or other heat exchange materials providing a suitable therapeutic effect are contemplated. Moreover, while a mitt has been shown, it is contemplated that a structure having individual finger compartments can be made in accordance with this invention.

Although certain presently preferred embodiments of the present invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What is claimed is:

1. A therapeutic cold pack for a human hand having a palm side and a back side comprising:
   a mitt-shaped structure for accommodating the human hand, said structure including
   a first plenum for covering the palm side of the hand comprised of two heat-sealed sheets;
   a second plenum structure for covering the back side of the hand comprised of two heat-sealed sheet;
   said first and second plenums heat sealed together so as to form an enclosure for the hand and to provide an opening in to which the hand may be inserted and removed;

finger structures for accommodating individual fingers; and a thumb structure for accommodating a thumb;

wherein said first and second plenums are filled with a paraffinic phase change material having a phase change temperature on the order of 50 degrees F. degrees;

and wherein said two heat-sealed sheets of said first plenum and said two heat-sealed sheets of said second plenum are so shaped as to form said finger structures for accommodating individual fingers and a thumb structure for accommodating the thumb.

2. A therapeutic cold pack as in claim 1, wherein said phase change material is opaque when in a solid state and translucent when in a liquid state.

3. A therapeutic cold pack as in claim 1, wherein said structure is comprised of a plastic sheet material.

4. A therapeutic cold pack as in claim 1, wherein said structure is comprised of a sheet material of a tripolymer.

5. A therapeutic cold pack as in claim 1, wherein said structure is comprised of a sheet material of polypropylene.

6. A therapeutic cold pack as in claim 1, which comprises a phase change material and holding structure for which the need for recharging by refrigeration is apparent by visual inspection.

7. A therapeutic cold pack as in claim 1, wherein said structure is shaped so as to fit either a right hand or a left hand.

\* \* \* \* \*

UNITED STATES PATENT AND TRADEMARK OFFICE
CERTIFICATE OF CORRECTION

PATENT NO. : 5,935,157
DATED      : August 10, 1999
INVENTOR(S): Susan HARMAN

It is certified that error appears in the above-indentified patent and that said Letters Patent is hereby corrected as shown below:

Title page, Item [76] "Harmon" should read --Harman--

Column 3, (claim 1), line 7, delete "degrees".

Signed and Sealed this

Ninth Day of May, 2000

Attest:

Q. TODD DICKINSON

*Attesting Officer*          *Director of Patents and Trademarks*